United States Patent [19]

Leininger et al.

[11] Patent Number: 4,725,689

[45] Date of Patent: Feb. 16, 1988

[54] PREPARATION OF 2-AMINO-3-CYANO-5-DIALKOXYMETHYL-PYRAZINES AND INTERMEDIATES FOR THIS METHOD

[75] Inventors: Hartmut Leininger, Neustadt; Wolfgang Littmann, Mannheim; Joachim Paust, Neuhofen, all of Fed. Rep. of Germany

[73] Assignee: BASF Aktiengesellschaft, Ludwigshafen, Fed. Rep. of Germany

[21] Appl. No.: 776,462

[22] Filed: Sep. 16, 1985

[30] Foreign Application Priority Data

Sep. 15, 1984 [DE] Fed. Rep. of Germany ....... 3433960

[51] Int. Cl.[4] ........................................... C07D 403/04
[52] U.S. Cl. .................................... 544/405; 544/336; 544/407
[58] Field of Search ........................ 544/336, 405, 402

[56] References Cited

U.S. PATENT DOCUMENTS 4,267,327 5/1981 Cozzi et al. ..................... 544/336

FOREIGN PATENT DOCUMENTS 1493752 11/1965 Fed. Rep. of Germany .

OTHER PUBLICATIONS

E. C. Taylor et al, J. Org. Chem., vol. 43, No. 4, 1978, p. 736.
E. C. Taylor et al, J. Org. Chem. 45, 1980, pp. 2485 to 2489.
E. C. Taylor et al, J. Org. Chem. 46, 1981, pp. 1394 to 1402.
E. J. Corey et al, *Tetrahedron Letters*, No. 31, pp. 2647 to 2650.
Georg Thieme Verlag, Stuttgart, 1962, pp. 728, 731, 748.

*Primary Examiner*—Donald G. Daus
*Assistant Examiner*—William A. Teoli, Jr.
*Attorney, Agent, or Firm*—Oblon, Fisher, Spivak, McClelland & Maier

[57] ABSTRACT

2-Amino-3-cyano-5-dialkoxymethylpyrazine derivatives of the general formula III

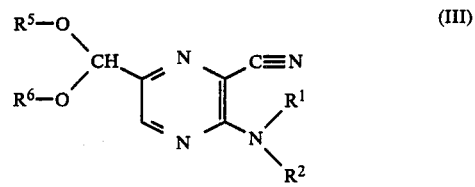

where $R^1$ and $R^2$ are each hydrogen or a protective group usually employed for amino groups and $R^5$ and $R^6$ are each alkyl of 1 to 4 carbon atoms, or together form an ethylene or propylene radical which is unsubstituted or substituted by methyl, are prepared starting from a novel 3-halomethyl-5-dihalomethyl-2-aminopyrazine derivative of the formula IV

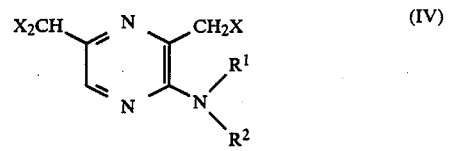

where X is Cl or Br, via a novel intermediate of the general formula I

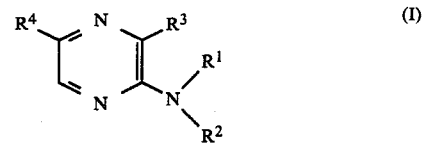

where $R^3$ is —CH$_2$—O—CO—CH$_3$ (a), —CH$_2$OH (b),

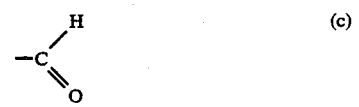

or —C≡N (d) and $R^4$ is —CHCl$_2$ or —CHBr$_2$ or, where $R^1$ and $R^2$ are each a protective group, $R^4$ may furthermore be

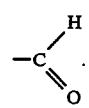

The compounds according to the invention are useful intermediates for the preparation of folic acid and active compounds derived from this.

2 Claims, No Drawings

PREPARATION OF 2-AMINO-3-CYANO-5-DIALKOXYMETHYLPYRAZINES AND INTERMEDIATES FOR THIS METHOD

The present invention relates to a process for the preparation of 2-amino-3-cyano-5-dialkoxymethylpyrazine derivatives, and 2-aminopyrazine derivatives substituted in the 3- and 5-positions, of the general formula I

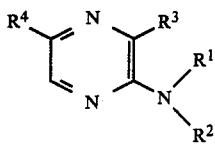

where $R^1$ and $R^2$ are each hydrogen or a protective group usually employed for amino groups, and may furthermore be bonded to one another, $R^3$ is —CH$_2$—O—CO—CH$_3$ (a), —CH$_2$OH (b),

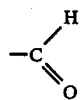

or —C≡N (d), and $R^4$ is —CHCl$_2$ or —CHBr$_2$, or, where $R^1$ and $R^2$ are each a protective group, $R^4$ is

as novel intermediates for this process.

The general object of the invention was to make the physiologically important compound folic acid

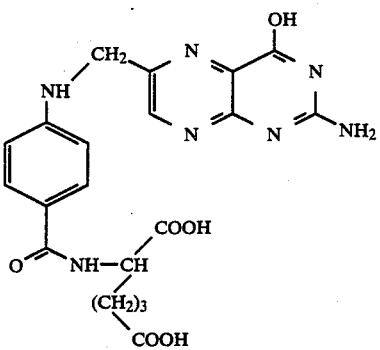

and its derivatives more readily accessible. The object related in particular to novel intermediates having the 2-aminopyrazine structure, which on the one hand are readily obtainable and on the other hand can be converted in a relatively simple manner to reactive pteridines and further to folic acid or its derivatives.

E. C. Taylor et al. (J. Org. Chem. 43 (1978), No. 4, 736-737) disclose that 6-formylpterin of the formula

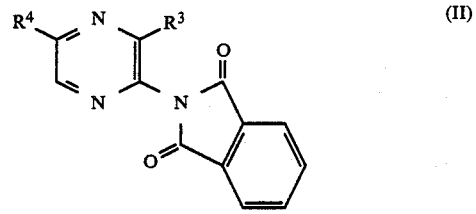

which is a key compound for folic acid and a very large variety of derivatives of this, can be prepared in a relatively simple manner and in good yields from 2-amino-3-cyano-5-dialkoxymethylpyrazine. However, the starting compound envisaged in this publication for the preparation of the 2-amino-3-cyano-5-dialkoxymethylpyrazine, ie. 2-amino-3-cyano-5-chloromethylpyrazine, is unfortunately itself not readily obtainable. It is obtained, for example, in only moderate yields from aminomalonitrile and β-chloropyruvaldoxime, which in turn can be prepared from ketene and is physiologically an extremely unpleasant substance which decomposes at room temperature with formation of hydrocyanic acid and is therefore unsuitable for an industrial reaction (cf. E. C. Taylor et al., J. Org. Chem. 38 (1973) 806). In spite of great efforts by E. C. Taylor et al. (cf. J. Org. Chem. 45 (1980), 2485-2489, and J. Org. Chem. 46 (1981), 1394-1402), it has not been possible to provide an industrially usable process for the preparation of pure, isomer-free 2-amino-3-cyano-5-dialkoxymethylpyrazines, so that to date the latter have only been known as substances which are difficult to obtain and can be prepared in poor yields, in a large number of stages and/or from expensive starting materials which are not readily synthesizable.

It is an object of the present invention to provide novel intermediates having the 2-aminopyrazine structure which on the same hand are readily obtainable and on the other hand can be converted in a relatively simple manner to 2-amino-3-cyano-5-dialkoxymethylpyrazine, thus permitting an advantageous overall process for the preparation of folic acid and its derivatives via 6-formylpterin.

We have found that this object is achieved, and that 2-amino-3-cyano-5-dialkoxymethylpyrazines are obtained in a surprisingly advantageous manner starting from novel 3-halomethyl-5-dihalomethyl-2-aminopyrazine derivatives via the novel 2-aminopyrazine derivatives substituted in the 3- and 5-positions, of the general formula I, in particular via the 2-phthalimidopyrazines substituted in the 3- and 5-positions, of the general formula II

where $R^3$ is —CH$_2$—O—CO—CH$_3$ (a), —CH$_2$OH (b), or —C≡N (d), and $R^4$ is —CHCl$_2$ or —CHBr$_2$.

The present invention therefore relates not only to the novel intermediates of the general formula I and in particular those of the general formula II, but also to a process for the preparation of 2-amino-3-cyano-5-dialkoxymethylpyrazine derivatives of the general formula III

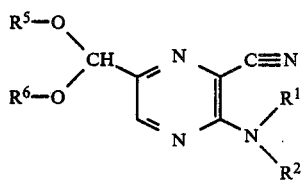

where $R^1$ and $R^2$ are each hydrogen or a protective group usually employed for amino groups, and may furthermore be bonded to one another, and $R^5$ and $R^6$ are each alkyl of 1 to 4 carbon atoms, or $R^5$ and $R^6$ together form an ethylene or propylene radical which is unsubstituted or substituted by methyl, wherein A. a novel 3-halomethyl-5-dihalomethyl-2-aminopyrazine derivative of the general formula IV

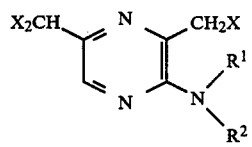

where X is Cl or Br, preferably Cl, is converted, either directly or via the novel 3-acetoxymethyl-5-dihalomethyl-2-aminopyrazine compound of the general formula Ia

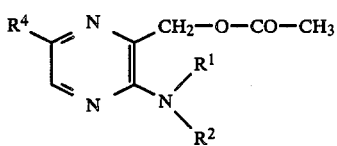

where $R^1$ and $R^2$ have the above meanings and $R^4$ is —CHCl$_2$ or —CHBr$_2$, preferably the former, to the novel 3-hydroxymethyl-5-dihalomethyl-2-aminopyrazine derivative of the general formula Ib

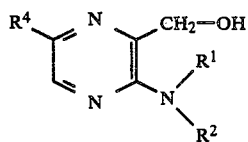

B. this is oxidized to the corresponding novel 3-formyl-5-dihalomethyl-2-aminopyrazine derivative of the general formula Ic

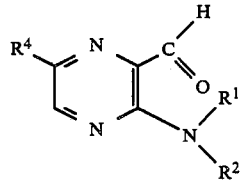

C. the latter is converted in a conventional manner to the corresponding novel 3-cyano-5-dihalomethyl-2-aminopyrazine derivative of the general formula Id

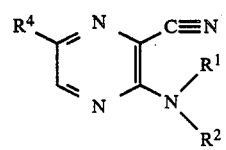

D. this is converted in a conventional manner to the corresponding 3-cyano-5-formyl-2-aminopyrazine derivative of the general formula Ie

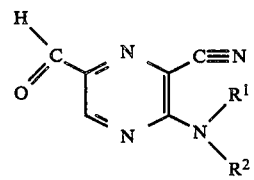

and

E. the latter is acetalized and, if necessary, the protective group is eliminated from the amino group.

In a very particularly advantageous process, 3-chloromethyl-5-dichloromethyl-2-phthalimidopyrazine (IVf) is used as the starting material.

In view of the prior art, it is very surprising that the compounds of the formula IV, in particular IVf, can be converted smoothly to the desired 2-amino-3-cyano-5-dialkoxymethylpyrazines of the formula III in very simple reaction steps, with high chemical yields and without the use of expensive and complicated chemicals.

The novel starting materials of the general formula IV can be prepared in relatively good yields by a process for which patent protection has been applied at the same time (cf. Patent Application No. P 34 33 959.0—O.Z. 0050/37335), by halogenation of the corresponding 2-amino-3,5-dimethylpyrazines, which in turn can advantageously be obtained by, for example, cyclization of α-iminodipropionitrile of the formula V

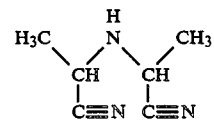

with a hydrogen halide. α-Iminodipropionitrile can be obtained by, for example, subjecting ammonia, acetaldehyde and hydrocyanic acid to the reaction described in German Laid-Open Application No. DOS 1,493,752.

The mixture of halogenation products obtained in the stated processes contains the desired isomer in an amount of from 60 to 70% when the process is carried out appropriately, and can be used as such.

REACTION STEP A

Conversion of the compounds of the formula IV to the corresponding 3-hydroxymethyl compounds Ib can be carried out in one step or via the novel 3-acetoxy compounds Ia. For the preparation via the 3-acetoxy compounds Ia, the compounds IV are dissolved in a polar organic solvent, such as dimethylformamide or, in particular, dimethyl sulfoxide, and reacted with an alkali metal acetate in the presence of glacial acetic acid under mild conditions, for example with prolonged stirring at room temperature, the product being obtained in good yield. The resulting product can be isolated and purified in a conventional manner without difficulty and can then be converted to the corresponding 3-hydroxymethyl compounds Ib in a transesterification reaction with a low-boiling alcohol, such as methanol, in the presence of an acidic catalyst, such as p-toluene-sulfonic acid, the methyl acetate formed being distilled off. If water, for example in an amount of from 3 to 20%, advantageously about 5%, based on the reaction mixture, is added to the reaction mixture described, which consists of IV, the solvent, glacial acetic acid and the alkali metal acetate, the 3-hydroxymethyl compound Ib is obtained directly under otherwise very similar conditions, the yield of the product after recrystallization being about 50%. The alcohol thus obtained can be isolated in a convenient and conventional manner, for example by extraction, and can be purified.

It is surprising that this step can be carried out in such an advantageous manner, and in particular that this reaction also takes place in only one reaction step and gives relatively good yields.

REACTION STEP B

Oxidation of the 3-hydroxymethyl compounds Ib to the novel 3-formyl compounds Ic must be carried out using an oxidizing agent which exclusively oxidizes the hydroxymethyl group to the formyl group, in a solvent which is insensitive to this oxidizing agent. The reaction takes place surprisingly advantageously with agents which effect oxidation under mild conditions, eg. pyridinium chlorochromate in a halohydrocarbon such as dichloromethane as a solvent. This method of oxidation is described in more detail in Tetrahedron Letters 1975, 2647.

REACTION STEP C

The conversion of the 3-formyl compounds Ic to the corresponding 3-cyano compounds Id is carried out in a conventional manner, so that a detailed description of the process is unnecessary. The reaction takes place particularly simply and without difficulty when Ic in a polar solvent, such as dimethyl sulfoxide, is first reacted with a hydroxylammonium salt, the oximino group is esterified with a conventional acylating agent, such as acetic anhydride, and the acetoximino-containing compound is then subjected to thermal decomposition in a fairly high-boiling solvent. This reaction too gives surprisingly good yields.

REACTION STEPS D AND E

The conversion of the 5-dihalomethyl-3-cyano compounds Id via the 5-formyl-3-cyano compounds Ie to the 5-dialkoxymethylpyrazine derivatives III is carried out in a conventional manner, so that detailed information is unnecessary.

The process according to the invention and the novel intermediates of the formula I provide for the first time a reaction route which can also be employed industrially and gives 2-amino-3-cyano-5-dialkoxymethylpyrazines and hence 6-formylpterin, a key compound for folic acid and active compounds derived from this.

EXAMPLE 1 a. Preparation of 3-acetoxymethyl-5-dichloromethyl-2-phthalimidopyrazine 50 ml of absolute glacial acetic acid and 35 g of potassium acetate were added to a solution of 57.7 g (0.16 mole) of 65% strength 3-chloromethyl-5-dichloromethyl-2-phthalimidopyrazine in 1,000 ml of dimethyl sulfoxide, and the mixture was then stirred for three days at room temperature. Thereafter, 1,000 ml of dichloromethane and 1,000 ml of ice-water were added to the reaction mixture, the resulting mixture was mixed thoroughly, and phase separation was effected. The aqueous phase was extracted once with 500 ml of dichloromethane and once with 250 ml of dichloromethane. The combined organic phases were washed twice with 1,000 ml of water, dried over sodium sulfate and evaporated down in a rotary evaporator. The blackish brown oil was taken up in 20 ml of methanol at the boil, and the solution was left to crystallize at room temperature. The product was then suspended in a little diethyl ether, filtered off and dried. The crystals were then recrystallized again from methanol. 30.6 g (77% of theory) of 3-acetoxymethyl-5-dichloromethyl-2-phthalimidopyrazine of melting point 117°–118° C. were obtained. $^1$H-NMR (270 MHz, CDCl$_3$): δ1.9 (s, 3H), 5.3 (s, 2H), 6.9 (s, 1H), 8.1 (m, 4H), 9.1 (s, 1H).

b. Preparation of 3-hydroxymethyl-5-dichloromethyl-2-phthalimidopyrazine

A mixture of 15 g (0.04 mole) of 3-acetoxymethyl-5-dichloromethyl-2-phthalimidopyrazine, 150 ml of methanol and 0.15 g of p-toluenesulfonic acid was heated to the boil, and a mixture of methanol and methyl acetate was slowly distilled off in the course of 5 hours. The mixture was then evaporated down to one-third of its total volume, and the precipitated crystals were isolated, and recrystallized from ethyl acetate. 7.18 g (54%) of 5-dichloromethyl-3-hydroxymethyl-2-phthalimidopyrazine of melting point 188°–189° C. were obtained. $^1$H-NMR (CDCl$_3$ 270 MHz): δ4.7 (s, 2H), 6.9 (s, 1H), 8.1 (m, 4H), 9.1 (s, 1H).

c. Preparation of 3-formyl-5-dichloromethyl-2-phthalimidopyrazine 5.1 g of pyridinium chlorochromate were added a little at a time to a solution of 4 g of 3-hydroxymethyl-5-dichloromethyl-2-phthalimidopyrazine in 80 ml of dichloromethane at 35° C., after which the mixture was stirred for 40 minutes and filtered over silica gel, and the filtrate was evaporated down. 3.1 g (76%) of colorless crystals of 3-formyl-5-dichloromethyl-2-phthalimidopyrazine of melting point 145°–146° C. (from ethyl acetate) were obtained. $^1$H-NMR (270 MHz, CDCl$_3$): δ6.9 (s, 1H), 8.0 (m, 4H), 9.3 (s, 1H), 10.1 (s, 1H).

d. Preparation of 3-oximino-5-dichloromethyl-2-phthalimidopyrazine

A solution of 10 g of 3-formyl-5-dichloromethyl-2-phthalimidopyrazine in 50 ml of dimethyl sulfoxide was heated at 50° C., 7 g of hydroxylamine hydrochloride were added, and the mixture was stirred for 15 minutes at 70° C. Thereafter, 700 ml of water were added to the reaction solution, the mixture was filtered and the filtrate was washed with a little diethyl ether. 6.8 g of colorless crystals (65%) of 3-oximinodichloromethyl-2-phthalimidopyrazine were obtained. $^1$H-NMR (270 MHz, DMSO-$d_6$): $\delta$7.7 (s, 1H), 8.0 (m, 4H), 8.3 (s, 1HO), 9.1 (s, 1H), 12.0 (s, OH).

e. Preparation of 3-acetoximino-5-dichloromethyl-2-phthalimidopyrazine

A suspension of 10 g of 3-oximino-5-dichloromethyl-2-phthalimidopyrazine in 15 ml of acetic anhydride was heated at 100° C., the suspension becoming a clear solution. The latter was then left for a further 15 minutes at 100° C., after which the reaction mixture was evaporated to dryness under reduced pressure. The resulting residue was recrystallized from absolute methanol. 10 g of 3-acetoximino-5-dichloromethyl-2-phthalimidopyrazine were obtained. $^1$H-NMR (270 MHz, DMSO-$d_6$): $\delta$1.9 and 2.1 (s, 3H in each case), 7.8 (s, 1H), 8.1 (m, 4H), 9.0 and 9.3 (s, 1H in each case), 9.5 (s, 1H).

f. Preparation of 3-cyano-5-dichloromethyl-2-phthalimidopyrazine

A solution of 10 g of 3-acetoximino-5-dichloromethyl-2-phthalimidopyrazine in 100 ml to 1,2-dichlorobenzene was refluxed for 60 minutes, after which the solvent was distilled off under $10^{-2}$ mbar, the residue was taken up in a little absolute methanol and the product was filtered off under suction. 8.1 g (95%) of 3-cyano-5-dichloromethyl-2-phthalimidopyrazine were obtained.

g. Preparation of 3-cyano-5-dimethoxymethyl-2-phthalimidopyrazine 5 ml of morpholine were carefully added dropwise to a solution of 3 g of 3-cyano-5-dichloromethyl-2-phthalimidopyrazine in 60 ml of dichloromethane, and the reaction mixture was refluxed gently for one hour. It was then cooled in an ice-bath and filtered under suction. The organic phase was evaporated down, the residue was taken up in methanol and 2 g of an activated acidic ion exchanger were added. The mixture was then refluxed for 2 hours and evaporated down, and the residue was chromatographed over silica gel. 1.5 g (51%) of 3-cyano-5-dimethoxymethyl-2-phthalimidopyrazine of melting point 115°–116° C. were obtained. $^1$H-NMR (270 MHz, CDCl$_3$): $\delta$3.5 (s, 6H), 5.5 (s, 1H), 8.0 (m, 4H), 9.1 (s, 1H).

h. Preparation of 2-amino-3-cyano-5-dimethoxymethylpyrazine 0.2 g of hydrazine hydrate were added dropwise to a suspension of 2 g of 3-cyano-5-dimethoxymethyl-2-phthalimidopyrazine in 40 ml of absolute methanol at 40° C. Immediately after the addition, the solution became clear, and crystals were precipitated after a few minutes. Chromatography over silica gel gave 0.9 g (75%) of 2-amino-3-cyano-5-dimethoxymethylpyrazine. $^1$H-NMR (270 MHz, DMSO-$d_6$): $\delta$3.3 (s, 6H), 5.0 (s, 1H), 8.35 (s, 1H).

EXAMPLE 2

Preparation of 5-dichloromethyl-3-hydroxymethyl-2-phthalimidopyrazine directly from 3-chloromethyl-5-dichloromethyl-2-phthalimidopyrazine 50 ml of glacial acetic acid and 35 g of potassium acetate were added to a solution of 57.7 g (0.16 mole) of 65% strength 3-chloromethyl-5-dichloromethyl-2-phthalimidopyrazine in 1,000 ml of a 95:5 dimethyl sulfoxide/water mixture. The mixture was stirred for three days at room temperature, after which 1,000 ml of dichloromethane and 1,000 ml of ice-water were added, the resulting mixture was mixed thoroughly and phase separation was effected. The aqueous phase was washed once with 500 ml of dichloromethane and once with 250 ml of dichloromethane, and the combined organic phases were washed twice with 1,000 ml of water, dried over sodium sulfate and evaporated down. The resulting black oil was brought to crystallization with 50 ml of methanol, and then recrystallized from 700 ml of methanol. 16.6 g (47%) of 5-dichloromethyl-3-hydroxymethyl-2-phthalimidopyrazine of melting point 191°–192° C. (sublimation with decomposition) were obtained. $^1$H-NMR (200 MHz, CDCl$_3$): $\delta$3.3 (t, OH), 4.8 (d, 2H), 6.9 (s, 1H), 8.0 (m, 4H), 9.1 (s, 1H).

We claim:

1. A 2-aminopyrazine derivative which is substituted in the 3- and 5-positions, of the formula I

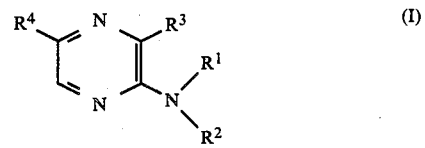

where $R^1$ and $R^2$ are each hydrogen or $R^1$ and $R^2$ together are the protective group,

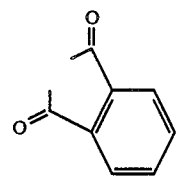

$R^3$ is —CH$_2$—O—CO—CH$_3$ (a), —CH$_2$OH (b),

or —C≡N (d) and $R^4$ is —CHCl$_2$ or —CHBr$_2$, or, where $R^1$ and $R^2$ are said protective group, $R^4$ may furthermore be

2. A 2-phthalimidopyrazine which is substituted in the 3- and 5-positions, of the formula II

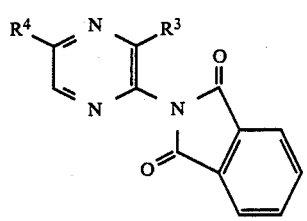
where $R^3$ is $-CH_2-OH$, $-CH_2-O-CO-CH_3$, 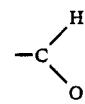 or $-C\equiv N$ and $R^4$ is $-CHCl_2$, $-CHBr_2$ or
—C(H)=O
* * * * *